(12) United States Patent
Yan et al.

(10) Patent No.: US 8,945,528 B2
(45) Date of Patent: Feb. 3, 2015

(54) USE OF INTERLEUKIN-22 IN TREATING VIRAL HEPATITIS

(75) Inventors: Xiaoqiang Yan, Shanghai (CN); Zhihua Huang, Shanghai (CN); Hongzhou Yang, Shanghai (CN); Yuliang Huang, Shanghai (CN)

(73) Assignee: Generon (Shanghai) Corporation Ltd. (CN)

( * ) Notice: Subject to any disclaimer, the term of this patent is extended or adjusted under 35 U.S.C. 154(b) by 0 days.

(21) Appl. No.: 13/819,717

(22) PCT Filed: Aug. 30, 2011

(86) PCT No.: PCT/CN2011/079124
§ 371 (c)(1),
(2), (4) Date: Feb. 28, 2013

(87) PCT Pub. No.: WO2012/028089
PCT Pub. Date: Mar. 8, 2012

(65) Prior Publication Data
US 2013/0171100 A1  Jul. 4, 2013

(30) Foreign Application Priority Data

Aug. 31, 2010 (CN) .......................... 2010 1 0268320

(51) Int. Cl.
*A61K 38/20* (2006.01)
*C07K 19/00* (2006.01)
*C07K 14/54* (2006.01)
*C12P 21/04* (2006.01)

(52) U.S. Cl.
CPC .................. *C07K 14/54* (2013.01); *A61K 38/20* (2013.01); *Y10S 514/883* (2013.01)
USPC ...... 424/85.2; 530/351; 530/387.3; 435/69.7; 435/320.1; 435/325; 435/327; 514/883

(58) Field of Classification Search
None
See application file for complete search history.

(56) References Cited

U.S. PATENT DOCUMENTS

| | | | |
|---|---|---|---|
| 6,331,613 | B1 | 12/2001 | Dumoutier et al. |
| 6,359,117 | B1 | 3/2002 | Dumoutier et al. |
| 6,551,799 | B2 | 4/2003 | Gurney et al. |
| 6,797,493 | B2 * | 9/2004 | Sun et al. .................... 435/69.7 |
| 7,307,161 | B1 | 12/2007 | Jacobs et al. |
| 7,459,533 | B2 | 12/2008 | Jacobs et al. |
| 7,585,646 | B2 | 9/2009 | Jacobs et al. |
| 7,666,402 | B2 | 2/2010 | Huang et al. |
| 7,696,158 | B2 | 4/2010 | Huang et al. |
| 7,718,604 | B2 | 5/2010 | Huang et al. |
| 7,972,833 | B2 | 7/2011 | Dumoutier et al. |
| 8,048,984 | B2 | 11/2011 | Jacobs et al. |
| 2009/0202475 | A1 | 8/2009 | Abbas et al. |
| 2011/0280828 | A1 | 11/2011 | Abbas et al. |
| 2013/0171100 | A1 | 7/2013 | Yan et al. |

FOREIGN PATENT DOCUMENTS

| | | |
|---|---|---|
| CN | 101168049 A | 4/2008 |
| CN | 101218254 A | 7/2008 |
| JP | 2008-508862 A | 3/2008 |
| WO | WO-02/029098 A2 | 4/2002 |
| WO | WO-2006/000448 A2 | 1/2006 |
| WO | WO-2006/000448 A3 | 1/2006 |
| WO | WO-2011/087986 A1 | 7/2011 |
| WO | WO-2012/028089 A1 | 3/2012 |

OTHER PUBLICATIONS

Radaeva et al, Hepatology 2004; vol. 39, pp. 1332-1342.*
Low et al, Human Reproduction, 2005, vol. 20, No. 7, pp. 1805-1813.*
International Search Report mailed on Dec. 8, 2011 for PCT Patent Application No. PCT/CN2011/079124, filed on Aug. 30, 2011, four pages.
Written Opinion of the International Searching Authority mailed on Dec. 8, 2011 for PCT Patent Application No. PCT/CN2011/079124, filed on Aug. 30, 2011, seven pages.
Xie, M.H. et al. (Oct. 6, 2000; e-pub. Jun. 29, 2000). "Interleukin (IL)-22, a novel human cytokine that signals through the interferon receptor-related proteins CRF2-4 and IL-22R," *J. Biol. Chem.* 275(40):31335-31339.
U.S. Appl. No. 12/672,274, filed Aug. 1, 2008, by Huang et al.
De Oliveira Neto, M. et al. (Mar. 1, 2008; e-pub. Nov. 16, 2007). "Interleukin-22 Forms Dimers That are Recognized by Two Interleukin-22R1 Receptor Chains," *Biophys. J.* 94(5):1754-1765.
Gao, B. (Apr. 2005). "Cytokines, STATs and Liver Disease," *Cell. Mol. Immunol.* 2(2):92-100.
Kotenko, S.V. et al. (Sep. 8, 1995). "Interaction Between the Components of the Interferon γ Receptor Complex," *J. Biol. Chem.* 270(36):20915-20921.
Pan, H. et al. (Feb. 2004). "Hydrodynamic Gene Delivery of Interleukin-22 Protects the Mouse Liver from Concanavalin A-, Carbon Tetrachloride-, and Fas Ligand-Induced Injury Via Activation of STAT3," *Cell. Mol. Immunol.* 1(1):43-49.
Zhu, H. et al. (Nov. 12, 2004). "STAT3 Induces Anti-Hepatitis C Viral Activity in Liver Cells," *Biochem. Biophys. Res. Commun.* 324(2):518-528.

* cited by examiner

*Primary Examiner* — Bridget E Bunner
*Assistant Examiner* — Fozia Hamud
(74) *Attorney, Agent, or Firm* — Morrison & Foerster LLP

(57) ABSTRACT

This invention relates to a use of IL-22 in the treatment of viral hepatitis. As illustrated in the examples of this invention, IL-22 can significantly reduce liver damage caused by hepatitis virus, and can significantly reduce the increase of transaminase ALT/AST induced by hepatitis virus. In addition, the IL-22 dimer of this invention can effectively treat viral hepatitis.

8 Claims, 4 Drawing Sheets

(Magnification×200)

SEQUENCE LISTING

<160> NUMBER OF SEQ ID NOS: 7

<210> SEQ ID NO 1
<211> LENGTH: 308
<212> TYPE: PRT
<213> ORGANISM: Artificial sequence
<220> FEATURE:
<221> NAME/KEY: misc_feature
<223> OTHER INFORMATION: IL-22 dimer

<400> SEQUENCE: 1

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Gly Ser Gly Gly Gly Ser Gly Gly Gly Gly Ser Gly Gly Gly
```

```
                145                 150                 155                 160
        Gly Ser Ala Pro Ile Ser Ser His Cys Arg Leu Asp Lys Ser Asn Phe
                        165                 170                 175

Gln Gln Pro Tyr Ile Thr Asn Arg Thr Phe Met Leu Ala Lys Glu Ala
                        180                 185                 190

Ser Leu Ala Asp Asn Asn Thr Asp Val Arg Leu Ile Gly Glu Lys Leu
                        195                 200                 205

Phe His Gly Val Ser Met Ser Glu Arg Cys Tyr Leu Met Lys Gln Val
                210                 215                 220

Leu Asn Phe Thr Leu Glu Glu Val Leu Phe Pro Gln Ser Asp Arg Phe
        225                 230                 235                 240

Gln Pro Tyr Met Gln Glu Val Val Pro Phe Leu Ala Arg Leu Ser Asn
                        245                 250                 255

Arg Leu Ser Thr Cys His Ile Glu Gly Asp Asp Leu His Ile Gln Arg
                        260                 265                 270

Asn Val Gln Lys Leu Lys Asp Thr Val Lys Lys Leu Gly Glu Ser Gly
                        275                 280                 285

Glu Ile Lys Ala Ile Gly Glu Leu Asp Leu Leu Phe Met Ser Leu Arg
                290                 295                 300

Asn Ala Cys Ile
        305

<210> SEQ ID NO 2
<211> LENGTH: 385
<212> TYPE: PRT
<213> ORGANISM: Artificial sequence
<220> FEATURE:
<221> NAME/KEY: misc_feature
<223> OTHER INFORMATION: IL-22 monomer with Fc fragment

<400> SEQUENCE: 2

Ala Pro Ile Ser Ser His Cys Arg Leu Asp Lys Ser Asn Phe Gln Gln
        1               5                   10                  15

Pro Tyr Ile Thr Asn Arg Thr Phe Met Leu Ala Lys Glu Ala Ser Leu
                        20                  25                  30

Ala Asp Asn Asn Thr Asp Val Arg Leu Ile Gly Glu Lys Leu Phe His
                        35                  40                  45

Gly Val Ser Met Ser Glu Arg Cys Tyr Leu Met Lys Gln Val Leu Asn
                50                  55                  60

Phe Thr Leu Glu Glu Val Leu Phe Pro Gln Ser Asp Arg Phe Gln Pro
        65                  70                  75                  80

Tyr Met Gln Glu Val Val Pro Phe Leu Ala Arg Leu Ser Asn Arg Leu
                        85                  90                  95

Ser Thr Cys His Ile Glu Gly Asp Asp Leu His Ile Gln Arg Asn Val
                        100                 105                 110

Gln Lys Leu Lys Asp Thr Val Lys Lys Leu Gly Glu Ser Gly Glu Ile
                        115                 120                 125

Lys Ala Ile Gly Glu Leu Asp Leu Leu Phe Met Ser Leu Arg Asn Ala
                130                 135                 140

Cys Ile Gly Ser Gly Gly Ser Gly Gly Gly Ser Gly Gly Gly
        145                 150                 155                 160

Gly Ser Val Glu Cys Pro Pro Cys Pro Ala Pro Pro Val Ala Gly Pro
                        165                 170                 175

Ser Val Phe Leu Phe Pro Pro Lys Pro Lys Asp Thr Leu Met Ile Ser
                        180                 185                 190
```

```
Arg Thr Pro Glu Val Thr Cys Val Val Val Asp Val Ser His Glu Asp
            195                 200                 205
Pro Glu Val Gln Phe Asn Trp Tyr Val Asp Gly Val Glu Val His Asn
        210                 215                 220
Ala Lys Thr Lys Pro Arg Glu Glu Gln Phe Asn Ser Thr Phe Arg Val
225                 230                 235                 240
Val Ser Val Leu Thr Val Val His Gln Asp Trp Leu Asn Gly Lys Glu
                245                 250                 255
Tyr Lys Cys Lys Val Ser Asn Lys Gly Leu Pro Ala Ser Ile Glu Lys
            260                 265                 270
Thr Ile Ser Lys Thr Lys Gly Gln Pro Arg Glu Pro Gln Val Tyr Thr
        275                 280                 285
Leu Pro Pro Ser Arg Glu Glu Met Thr Lys Asn Gln Val Ser Leu Thr
290                 295                 300
Cys Leu Val Lys Gly Phe Tyr Pro Ser Asp Ile Ala Val Glu Trp Glu
305                 310                 315                 320
Ser Asn Gly Gln Pro Glu Asn Asn Tyr Lys Thr Thr Pro Pro Met Leu
                325                 330                 335
Asp Ser Asp Gly Ser Phe Phe Leu Tyr Ser Lys Leu Thr Val Asp Lys
            340                 345                 350
Ser Arg Trp Gln Gln Gly Asn Val Phe Ser Cys Ser Val Met His Glu
        355                 360                 365
Ala Leu His Asn His Tyr Thr Gln Lys Ser Leu Ser Leu Ser Pro Gly
370                 375                 380
Lys
385

<210> SEQ ID NO 3
<211> LENGTH: 375
<212> TYPE: PRT
<213> ORGANISM: Artificial sequence
<220> FEATURE:
<221> NAME/KEY: misc_feature
<223> OTHER INFORMATION: IL-22 monomer with Fc fragment

<400> SEQUENCE: 3

Ala Pro Ile Ser Ser His Cys Arg Leu Asp Lys Ser Asn Phe Gln Gln
1               5                   10                  15
Pro Tyr Ile Thr Asn Arg Thr Phe Met Leu Ala Lys Glu Ala Ser Leu
            20                  25                  30
Ala Asp Asn Asn Thr Asp Val Arg Leu Ile Gly Glu Lys Leu Phe His
        35                  40                  45
Gly Val Ser Met Ser Glu Arg Cys Tyr Leu Met Lys Gln Val Leu Asn
    50                  55                  60
Phe Thr Leu Glu Glu Val Leu Phe Pro Gln Ser Asp Arg Phe Gln Pro
65                  70                  75                  80
Tyr Met Gln Glu Val Val Pro Phe Leu Ala Arg Leu Ser Asn Arg Leu
                85                  90                  95
Ser Thr Cys His Ile Glu Gly Asp Asp Leu His Ile Gln Arg Asn Val
            100                 105                 110
Gln Lys Leu Lys Asp Thr Val Lys Lys Leu Gly Glu Ser Gly Glu Ile
        115                 120                 125
Lys Ala Ile Gly Glu Leu Asp Leu Leu Phe Met Ser Leu Arg Asn Ala
130                 135                 140
Cys Ile Ala Ser Thr Lys Gly Pro Val Glu Cys Pro Pro Cys Pro Ala
145                 150                 155                 160
```

```
Pro Pro Val Ala Gly Pro Ser Val Phe Leu Phe Pro Lys Pro Lys
            165                 170                 175

Asp Thr Leu Met Ile Ser Arg Thr Pro Glu Val Thr Cys Val Val Val
            180                 185                 190

Asp Val Ser His Glu Asp Pro Glu Val Gln Phe Asn Trp Tyr Val Asp
            195                 200                 205

Gly Val Glu Val His Asn Ala Lys Thr Lys Pro Arg Glu Glu Gln Phe
    210                 215                 220

Asn Ser Thr Phe Arg Val Val Ser Val Leu Thr Val Val His Gln Asp
225                 230                 235                 240

Trp Leu Asn Gly Lys Glu Tyr Lys Cys Lys Val Ser Asn Lys Gly Leu
            245                 250                 255

Pro Ala Ser Ile Glu Lys Thr Ile Ser Lys Thr Lys Gly Gln Pro Arg
            260                 265                 270

Glu Pro Gln Val Tyr Thr Leu Pro Pro Ser Arg Glu Glu Met Thr Lys
    275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Met Leu Asp Ser Asp Gly Ser Phe Phe Leu Tyr Ser
            325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly Lys
    370                 375

<210> SEQ ID NO 4
<211> LENGTH: 385
<212> TYPE: PRT
<213> ORGANISM: Artificial sequence
<220> FEATURE:
<221> NAME/KEY: misc_feature
<223> OTHER INFORMATION: IL-22 monomer with Fc fragment

<400> SEQUENCE: 4

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
```

```
                    130                 135                 140
        Val Lys Gly Phe Tyr Pro Ser Asp Ile Ala Val Glu Trp Glu Ser Asn
        145                 150                 155                 160

Gly Gln Pro Glu Asn Asn Tyr Lys Thr Thr Pro Pro Met Leu Asp Ser
                        165                 170                 175

Asp Gly Ser Phe Phe Leu Tyr Ser Lys Leu Thr Val Asp Lys Ser Arg
                    180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys Gly
            210                 215                 220

Ser Gly Gly Gly Ser Gly Gly Gly Ser Gly Gly Gly Gly Ser Gly Ala
        225                 230                 235                 240

Pro Ile Ser Ser His Cys Arg Leu Asp Lys Ser Asn Phe Gln Gln Pro
                        245                 250                 255

Tyr Ile Thr Asn Arg Thr Phe Met Leu Ala Lys Glu Ala Ser Leu Ala
                    260                 265                 270

Asp Asn Asn Thr Asp Val Arg Leu Ile Gly Glu Lys Leu Phe His Gly
                275                 280                 285

Val Ser Met Ser Glu Arg Cys Tyr Leu Met Lys Gln Val Leu Asn Phe
        290                 295                 300

Thr Leu Glu Glu Val Leu Phe Pro Gln Ser Asp Arg Phe Gln Pro Tyr
        305                 310                 315                 320

Met Gln Glu Val Val Pro Phe Leu Ala Arg Leu Ser Asn Arg Leu Ser
                        325                 330                 335

Thr Cys His Ile Glu Gly Asp Asp Leu His Ile Gln Arg Asn Val Gln
                    340                 345                 350

Lys Leu Lys Asp Thr Val Lys Lys Leu Gly Glu Ser Gly Glu Ile Lys
                355                 360                 365

Ala Ile Gly Glu Leu Asp Leu Leu Phe Met Ser Leu Arg Asn Ala Cys
        370                 375                 380

Ile
        385

<210> SEQ ID NO 5
<211> LENGTH: 375
<212> TYPE: PRT
<213> ORGANISM: Artificial sequence
<220> FEATURE:
<221> NAME/KEY: misc_feature
<223> OTHER INFORMATION: IL-22 monomer with Fc fragment

<400> SEQUENCE: 5

Val Glu Cys Pro Pro Cys Pro Ala Pro Val Ala Gly Pro Ser Val
        1               5                   10                  15

Phe Leu Phe Pro Pro Lys Pro Lys Asp Thr Leu Met Ile Ser Arg Thr
                        20                  25                  30

Pro Glu Val Thr Cys Val Val Val Asp Val Ser His Glu Asp Pro Glu
                    35                  40                  45

Val Gln Phe Asn Trp Tyr Val Asp Gly Val Glu Val His Asn Ala Lys
                50                  55                  60

Thr Lys Pro Arg Glu Glu Gln Phe Asn Ser Thr Phe Arg Val Val Ser
        65                  70                  75                  80

Val Leu Thr Val Val His Gln Asp Trp Leu Asn Gly Lys Glu Tyr Lys
                        85                  90                  95
```

```
Cys Lys Val Ser Asn Lys Gly Leu Pro Ala Ser Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Ala
    210                 215                 220

Ser Thr Lys Gly Pro Ala Pro Ile Ser Ser His Cys Arg Leu Asp Lys
225                 230                 235                 240

Ser Asn Phe Gln Gln Pro Tyr Ile Thr Asn Arg Thr Phe Met Leu Ala
                245                 250                 255

Lys Glu Ala Ser Leu Ala Asp Asn Asn Thr Asp Val Arg Leu Ile Gly
            260                 265                 270

Glu Lys Leu Phe His Gly Val Ser Met Ser Glu Arg Cys Tyr Leu Met
        275                 280                 285

Lys Gln Val Leu Asn Phe Thr Leu Glu Glu Val Leu Phe Pro Gln Ser
290                 295                 300

Asp Arg Phe Gln Pro Tyr Met Gln Glu Val Val Pro Phe Leu Ala Arg
305                 310                 315                 320

Leu Ser Asn Arg Leu Ser Thr Cys His Ile Glu Gly Asp Asp Leu His
                325                 330                 335

Ile Gln Arg Asn Val Gln Lys Leu Lys Asp Thr Val Lys Lys Leu Gly
            340                 345                 350

Glu Ser Gly Glu Ile Lys Ala Ile Gly Glu Leu Asp Leu Leu Phe Met
        355                 360                 365

Ser Leu Arg Asn Ala Cys Ile
    370                 375

<210> SEQ ID NO 6
<211> LENGTH: 1278
<212> TYPE: DNA
<213> ORGANISM: Artificial sequence
<220> FEATURE:
<221> NAME/KEY: misc_feature
<223> OTHER INFORMATION: DNA sequence encoding IL-22 monomer with
      Fc fragment

<400> SEQUENCE: 6
gaattcccca gacccatggc cgccctgcag aaatctgtga gctctttcct tatggggacc      60
ctggccacca gctgcctcct tctcttggcc ctcttggtac agggaggagc agctgcgccc     120
atcagctccc actgcaggct tgacaagtcc aacttccagc agccctatat caccaaccgc     180
accttcatgc tggctaagga ggctagcttg gctgataaca cacagacgt cgtctcatt     240 ggggagaaac tgttccacgg agtcagtatg agtgagcgct gctatctgat gaagcaggtg     300
ctgaacttca cccttgaaga agtgctgttc cctcaatctg ataggttcca gcctatatg     360 caggaggtgg tgcccttcct ggccaggctc agcaacaggc taagcacatg tcatattgaa     420
```

```
ggtgatgacc tgcatatcca gaggaatgtg caaaagctga aggacacagt gaaaaagctt      480
ggagagagtg gagagatcaa agcaattgga gaactggatt tgctgtttat gtctctgaga      540
aatgcctgca ttggatccgg tggcggttcc ggtggaggcg aagcggcgg tggaggatca       600 gtcgagtgcc caccgtgccc agcaccacct gtggcaggac cgtcagtctt cctcttcccc      660
ccaaaaccca aggacaccct catgatctcc cggacccctg aggtcacgtg cgtggtggtg      720
gacgtgagcc acgaagaccc cgaggtccag ttcaactggt acgtggacgg cgtggaggtg      780
cataatgcca agacaaagcc acgggaggag cagttcaaca gcacgttccg tgtggtcagc      840
gtcctcaccg ttgtgcacca ggactggctg aacggcaagg agtacaagtg caaggtctcc      900
aacaaaggcc tcccagcctc catcgagaaa accatctcca aaaccaaagg cagccccga       960 gaaccacagg tgtacaccct gcccccatcc cgggaggaga tgaccaagaa ccaggtcagc     1020
ctgacctgcc tggtcaaagg cttctacccc agcgacatcg ccgtggagtg ggagagcaat     1080
gggcagccgg agaacaacta caagaccaca cctcccatgc tggactccga cggctccttc     1140
ttcctctaca gcaagctcac cgtggacaag agcaggtggc agcaggggaa cgtcttctca     1200
tgctccgtga tgcatgaggc tctgcacaac cactacacgc agaagagcct ctccctgtct     1260
ccgggtaaat gatctaga                                                   1278

<210> SEQ ID NO 7
<211> LENGTH: 1248
<212> TYPE: DNA
<213> ORGANISM: Artificial sequence
<220> FEATURE:
<221> NAME/KEY: misc_feature
<223> OTHER INFORMATION: DNA sequence encoding IL-22 monomer with Fc
      fragment

<400> SEQUENCE: 7
gaattcccca gacccatggc cgccctgcag aaatctgtga gctctttcct tatggggacc       60
ctggccacca gctgcctcct tctcttggcc ctcttggtac agggaggagc agctgcgccc      120
atcagctccc actgcaggct tgacaagtcc aacttccagc agcccctatat caccaaccgc     180 accttcatgc tggctaagga ggctagcttg gctgataaca cacagacgt tcgtctcatt       240 ggggagaaac tgttccacgg agtcagtatg agtgagcgct gctatctgat gaagcaggtg      300
ctgaacttca cccttgaaga agtgctgttc cctcaatctg ataggttcca gccttatatg      360
caggaggtgg tgcccttcct ggccaggctc agcaacaggc taagcacatg tcatattgaa      420
ggtgatgacc tgcatatcca gaggaatgtg caaaagctga aggacacagt gaaaaagctt      480
ggagagagtg gagagatcaa agcaattgga gaactggatt tgctgtttat gtctctgaga      540
aatgcctgca ttgccagcac aaagggacca gtcgagtgcc accgtgccc agcaccacct      600 gtggcaggac cgtcagtctt cctcttcccc ccaaaaccca aggacaccct catgatctcc      660
cggacccctg aggtcacgtg cgtggtggtg gacgtgagcc acgaagaccc cgaggtccag      720
ttcaactggt acgtggacgg cgtggaggtg cataatgcca agacaaagcc acgggaggag      780
cagttcaaca gcacgttccg tgtggtcagc gtcctcaccg ttgtgcacca ggactggctg      840
aacggcaagg agtacaagtg caaggtctcc aacaaaggcc tcccagcctc catcgagaaa      900
accatctcca aaaccaaagg cagccccga gaaccacagg tgtacaccct gcccccatcc      960
cgggaggaga tgaccaagaa ccaggtcagc ctgacctgcc tggtcaaagg cttctacccc     1020
agcgacatcg ccgtggagtg ggagagcaat gggcagccgg agaacaacta caagaccaca     1080
```

```
cctcccatgc tggactccga cggctccttc ttcctctaca gcaagctcac cgtggacaag    1140
agcaggtggc agcaggggaa cgtcttctca tgctccgtga tgcatgaggc tctgcacaac    1200
cactacacgc agaagagcct ctccctgtct ccgggtaaat gatctaga                1248
```

USE OF INTERLEUKIN-22 IN TREATING VIRAL HEPATITIS

REFERENCE TO SEQUENCE LISTING

The hard copy of the sequence listing submitted herewith and the corresponding computer readable form are both incorporated herein by reference in their entireties.

FIELD OF INVENTION

This invention relates to the area of biological and medical technologies; in particular, this invention relates to the use of interleukin-22 in the treatment of viral hepatitis.

BACKGROUND OF INVENTION

Viral hepatitis is an inflammation of the liver caused by hepatitis A, B, C, D, or E virus. All hepatitis viruses can cause acute hepatitis; further, hepatitis B, C, or D can even cause chronic hepatitis which can lead to cirrhosis, liver failure and liver cancer.

For example, in the United States, there are about 500 to 600 thousand new cases of viral hepatitis, in which hepatitis A, an acute disease caused by hepatitis A virus, accounts for 150 thousand cases. Meanwhile, there is an increase of 200 to 300 thousand new cases of hepatitis B, in which about 6 to 10% of hepatitis B cases develop into chronic hepatitis B. Chronic hepatitis B cases can easily be converted into cirrhosis, liver failure and liver cancer. It is estimated that there are about 200 to 300 million chronic hepatitis B cases throughout the world and in which the United States accounts for 1.2 million cases. Hepatitis B is caused by hepatitis B virus. Besides, there are about 150 thousand new cases of hepatitis C each year (hepatitis C was previously known as non-A non-B hepatitis). About 50 to 70% of acute hepatitis C cases are converted into chronic hepatitis C cases and chronic hepatitis C cases can easily be converted into cirrhosis, liver failure and liver cancer. It is estimated that there are about 3.5 million chronic hepatitis C cases in the United States. Both chronic hepatitis B and C cases can be converted into chronic hepatitis. Under the condition of chronic hepatitis, the hepatitis virus would continue to live and duplicate within the liver for a long period of time, which would at the same time cause chronic inflammation of the liver, leading to cirrhosis, liver failure and liver cancer.

For example, in China, there are 500 to 600 thousand new cases of viral hepatitis in which hepatitis A accounts for 150 thousand cases.

Diagnosis of viral hepatitis is based on detection of the presence of antibodies against the virus, viral genetic material, viral protein and antigen. The important biomarkers on the development of liver tissue damage derived from hepatitis is the increase in activity of blood enzymes and transaminase, such as aspartate aminotransferase (AST or S (GOT)), and alanine aminotransferase (ALT or SGPT).

The methods of treating acute and chronic hepatitis are different. For the treatment of acute viral hepatitis (hepatitis A), the first step to do is to alleviate the symptoms of nausea, vomiting and abdominal pain of the patient. Currently there is no cure for hepatitis A from the clinical perspective, and the therapy is focused on ensuring that patients have the sufficient nutritional supplements and on avoiding permanent liver injury. Patients with acute hepatitis can be treated with immunoglobulin within 2 weeks of the onset of the disease. The main treatment for chronic hepatitis B cases is interferon (interferon α-2b or interferon A) and pegylated interferon α-2a (Pegasys), as well as antiviral drugs such as telbivudine (Tyzeka), entecavir (Baraclude), lamivudine (Epivir-HBV), and adefovir dipivoxil (Hepsera). The main treatment for chronic hepatitis C cases is antivirals and interferon or interferon compound, such as pegylated interferon α-2a and pegylated interferon α-2b in combination with the antiviral drug ribavirin. Nowadays, there is no effective drug for treating liver damage caused by virus.

IL-22, also known as interleukin-10 related T cell-derived inducible factor (IL-TIF), is a glycoprotein secreted by T cells. The expression of IL-22 mRNA was originally demonstrated in IL-9-stimulated T cell lines, IL-9-stimulated mast cell line, as well as concanavalinA activated spleen cells of mouse. The human IL-22 mRNA is mainly expressed in isolated peripheral T cells and are upon stimulation by anti-CD-3 antibody or ConA. IL-22 mRNA is also expressed in the stimulated NK cells. Activated T cells are mainly CD4+ cells, especially Th1 cells via the CD28 pathway.

IL-22 precursor is composed of 179 amino acid residues (the mature peptide is composed of 146 amino acid residues). Dumoutier first reported the IL-22 DNA sequences of cloned mouse and human (Dumoutier, et al, *JI* 164:1814-1819, 2000). In addition, Dumoutier owned the patents related to IL-22 (U.S. Pat. No. 6,359,117 and U.S. Pat. No. 6,274,710), whereas Gurney owned the patent related to use of IL-22 in the treatment of human pancreatic disease (U.S. Pat. No. 6,551,799).

IL-22 is mainly expressed in thymus, brain, activated T cells and mast cells, the lectin-stimulated spleen cells (Duroutier *JI* 2002), interleukin-2/interleukin-12-stimulated NK cells (Wolk, K *JI* 2002), and in a number of organs and tissues, including gut, liver, stomach, kidney, lung, heart, thymus, spleen, upon LPS stimulation (Dumoutier PNAS paper), in which an increase of the expression of IL-22 in those organs and tissues can be measured.

IL-22 expresses its biological function through the combination of IL-22R1 receptor and IL-10R2 receptor. IL-22R1 is a receptor specific to IL-22 and is expressed in skin, kidney, the digestive system (pancreas, small intestine, liver, large intestine, colon), and the respiratory system (lung, bronchi). The research on IL-22 as a regulatory agent to the immune system has been published.

The medical use of IL-22 in reducing serum triglycerides and obesity has been reported in patent applications related to the medical uses of IL-22 (See WO 2006/073 508 and CN 200510023103.0).

However, it has not yet been discovered that IL-22 can play an active role in the treatment of viral hepatitis.

SUMMARY OF INVENTION

In the light of the foregoing background, it is an object of the present invention to provide an alternate drug for the treatment of viral hepatitis with improved efficacy and the use thereof, i.e. the use of interleukin-22 (IL-22) in the treatment of viral hepatitis in mammals.

Accordingly, the present invention, in one aspect, provides a use of human IL-22 or a dimer thereof in the manufacture of a drug for treating viral hepatitis.

In an exemplary embodiment of the present invention, the viral hepatitis comprises hepatitis A, hepatitis B, hepatitis C, hepatitis D, and hepatitis E.

In another exemplary embodiment, the human IL-22 dimer is shown as formula (I):

$$M1-L-M2 \quad (I)$$

wherein

M1 is a first human IL-22 monomer;

M2 is a second human IL-22 monomer; and

L is a linker connecting the first monomer and the second monomer and disposed there between, wherein, the IL-22 dimer retains the biological activity of IL-22 and has a serum half-life of at least twice of the half-life of either the first or the second monomer.

In an exemplary embodiment of the present invention, the linker L is selected from the group consisting of:

i). a short peptide comprising 3 to 50 amino acids; and ii). a polypeptide of formula (II):

—Z—Y—Z—  (II)

wherein

Y is a carrier protein;

Z is null, or a short peptide(s) comprising 1 to 30 amino acids;

"—" is a chemical bond or a covalent bond.

In another exemplary embodiment, the first monomer and the second monomer are of the same entity.

In another exemplary embodiment, the first monomer and the second monomer are of the different entities.

In an exemplary embodiment, the biological activity includes:

(a). Reducing the chance of liver inflammation and hepatocellular necrosis, and protecting liver cells from damage caused by hepatitis virus; and (b). inhibiting the increase of ALT/AST caused by the hepatitis virus.

In another exemplary embodiment, the carrier protein is formed by the connection of two Fc fragments of IgG via disulfide bond. In another exemplary embodiment, there are 2-4 disulfide bonds between the two Fc fragments.

In another exemplary embodiment, the carrier protein is albumin or Fc fragment of human IgG.

In another exemplary embodiment, the "—" is a peptide bond.

In one exemplary embodiment, the serum half-life of the IL-22 dimer is at least three, five, or ten times of the half-life of the first and/or the second monomer.

In another exemplary embodiment, the IL-22 dimer is a dimer formed by monomers in which the monomer comprises an amino acid sequence selected from the group consisting of SEQ ID NOs: 2-5.

According to another aspect of the present invention, a human IL-22 dimer of formula (I) is provided:

M1-L-M2  (I)

wherein

M1 is a first human IL-22 monomer;

M2 is a second human IL-22 monomer; and

L is a linker connecting the first monomer and the second monomer and disposed there between, wherein, the IL-22 dimer retains the biological activity of IL-22 and has a serum half-life of at least twice of the half-life of either the first or the second monomer.

In the third aspect of the present invention, a pharmaceutical composition for treating viral hepatitis is provided, which comprises a pharmaceutically acceptable carrier and a human IL-22 dimer of formula (I):

M1-L-M2  (I)

wherein

M1 is a first human IL-22 monomer;

M2 is a second human IL-22 monomer; and

L is a linker connecting the first monomer and the second monomer and disposed there between, wherein, the IL-22 dimer retains the biological activity of IL-22 and has a serum half-life of at least twice of the half-life of either the first or the second monomer.

In another exemplary embodiment, the IL-22 dimer is a dimer formed by monomers in which the monomer comprises an amino acid sequence selected from the group consisting of SEQ ID NOs: 3 and 5.

In a further aspect of the present invention, a method of preparing IL-22 dimer comprises the steps of:

a) transforming mammalian cells with an expression vector comprising a DNA sequence encoding a IL-22-Fc complex;

b) culturing the transformed mammalian cells; and c) isolating and purifying the IL-22 dimer obtained from step (b).

It is clear for a skilled person in the art that, the technical features mentioned above and discussed in the examples below of the present invention could be combined with each other to result in a new or even better technical solution. Hence this invention should not be construed as limited to the embodiments set forth herein.

In a specific embodiment, the amino acid sequence of the IL-22 dimer is shown in SEQ ID NO:1 in which amino residues 1-146 represent IL-22, amino residues 147-162 represent the linker, and residues 163-308 represent another IL-22.

Figure 2A:
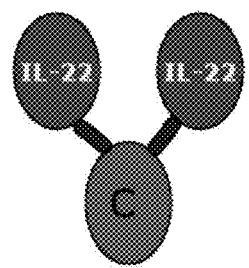
Figure 2B:
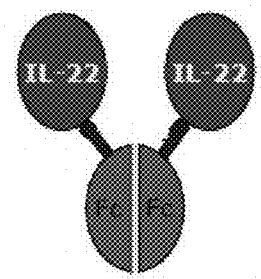

FIGS. 2A and 2B illustrate the structure of an IL-22 dimer of the present invention in which "—" represents the amino acid linker and the oval-shaped object labeled with "IL-22" represents an IL-22 monomer. The oval-shaped object labeled with "C" represents a carrier protein in which the IL-22 monomer is disposed at the N-terminal of the carrier protein. The coupling of two Fc fragments via disulfide bond is also shown in FIG. 2B.

The amino acid sequence of an IL-22 monomer with Fc fragments, which is used to form the IL-22 dimer of this embodiment, is shown in SEQ ID NO:2 in which amino residues 1-146 represent an IL-22, amino residues 147-162 represent the linker, and residues 163-385 represent Fc fragment of human IgG2. An IL-22 dimer is formed by two IL-22 monomers with Fc fragments via the coupling of the Fc fragments.

The amino acid sequence of an IL-22 monomer with Fc fragments, which is used to form the IL-22 dimer of this embodiment, is shown in SEQ ID NO:3 in which amino residues 1-146 represent an IL-22, amino residues 147-152 represent the linker, and residues 153-375 represent Fc fragment of human IgG2. An IL-22 dimer is formed by two IL-22 monomers with Fc fragments via the coupling of the Fc fragments.

Figure 3A:
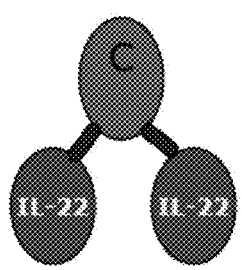
Figure 3B:
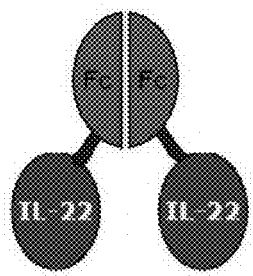

FIGS. 3A and 3B illustrate the structure of an IL-22 dimer of the present invention in which "—" represents the amino acid linker, the oval-shaped object labeled with "IL-22" represents an IL-22 monomer, the oval-shaped object labeled with "C" represents a carrier protein in which the IL-22 monomer is disposed at the C-terminal of the carrier protein. The coupling of two Fc fragments via disulfide bond is also shown in FIG. 3B.

The amino acid sequence of an IL-22 monomer with Fc fragments, which is used to form the IL-22 dimer of this embodiment, is shown in SEQ ID NO:4 in which amino residues 1-223 represent Fc fragment of human IgG2, amino residues 224-239 represent the linker, and residues 240-385 represent an IL-22. An IL-22 dimer is formed by two IL-22 monomers with Fc fragments via the coupling of the Fc fragments.

The amino acid sequence of an IL-22 monomer with Fc fragments, which is used to form the IL-22 dimer of this embodiment, is shown in SEQ ID NO:5 in which amino residues 1-223 represent Fc fragment of human IgG2, amino residues 224-229 represent the linker, and residues 230-375 represent an IL-22. An IL-22 dimer is formed by two IL-22 monomers with Fc fragments via the coupling of the Fc fragments.

Figure 4:
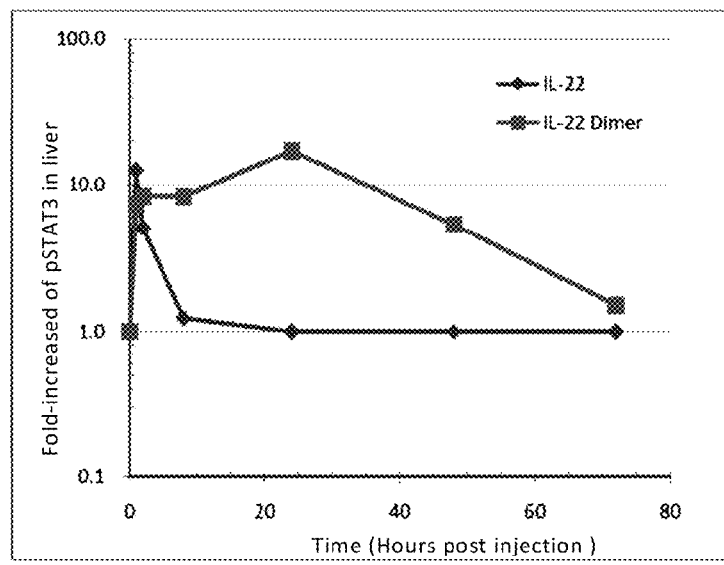

FIG. 4 shows the effect of IL-22 and IL-22 dimer (IL-22-Fc) on stimulating liver STAT3 of mice. The result illustrated that the stimulation bioactivity of IL-22 dimer was obviously higher than the stimulation bioactivity of IL-22.

Figure 5:
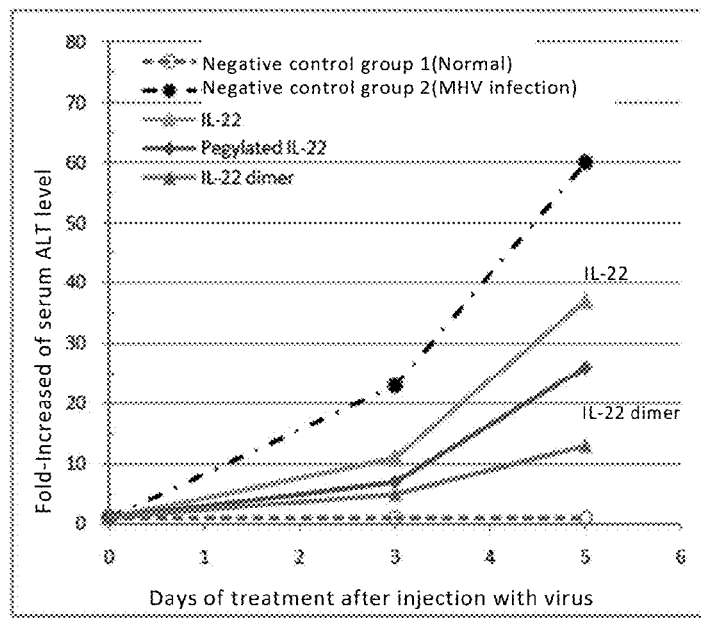

FIG. 5 shows the change on the serum ALT levels of the mice infected with hepatitis virus. Recombinant human IL-22 monomer (IL-22, pegylated IL-22) and IL-22 dimer was shown to inhibit the elevation of ALT levels caused by hepatitis virus, in which the inhibitory effect of IL-22 dimer is particularly significant.

Figure 6:
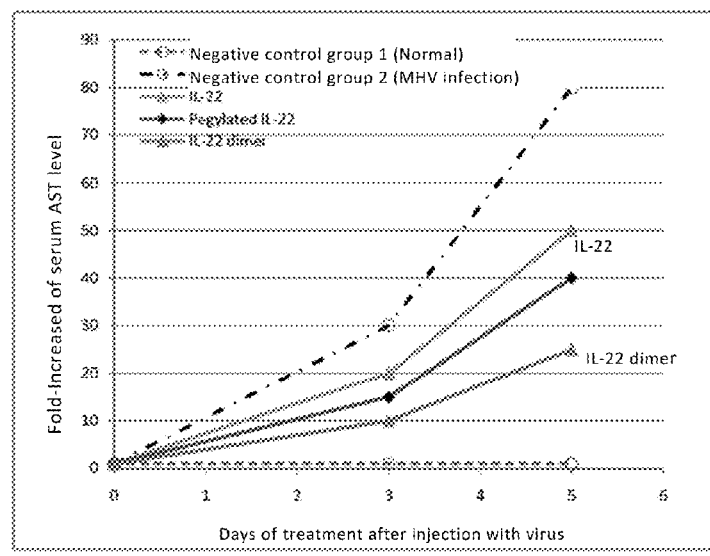

FIG. 6 shows the change on the serum AST levels of the mice infected with hepatitis virus. Recombinant human IL-22 monomer (IL-22, pegylated IL-22) and IL-22 dimer was shown to obviously inhibit the elevation of AST levels caused by hepatitis virus, in which the inhibitory effect of IL-22 dimer is particularly significant.

Figure 7:
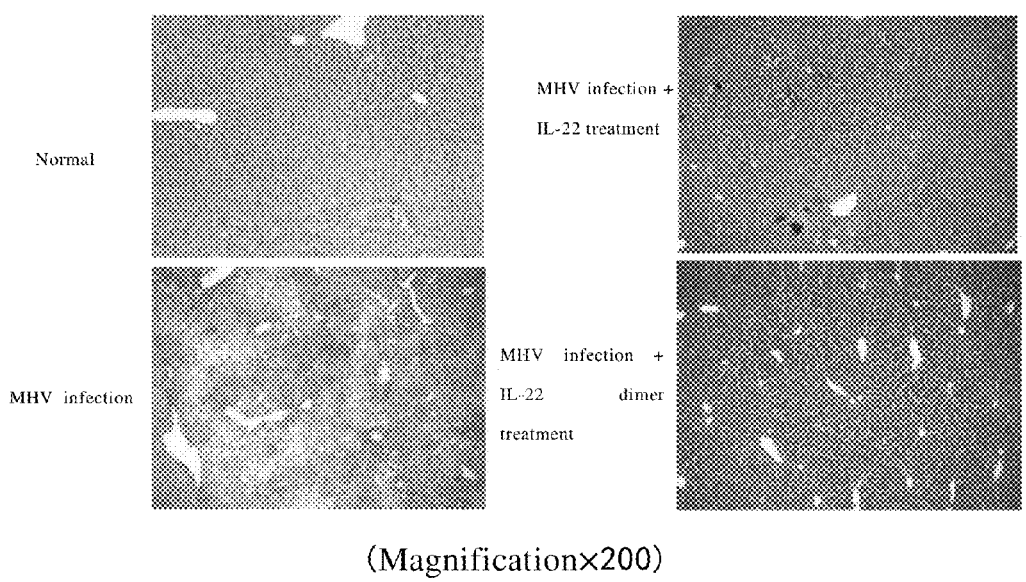

FIG. 7 shows the morphological changes of the liver histology of the mice infected with the hepatitis virus. Five days upon the infection of mice with MHV-A59 virus, severe inflammation of the liver tissue, cell necrosis, and abnormal morphological changes were observed. Upon treatment with IL-22 or its dimer, the morphology of the liver histology of the animals was obviously protected, with a significant decrease in inflammation and cell necrosis.

Figure 8:
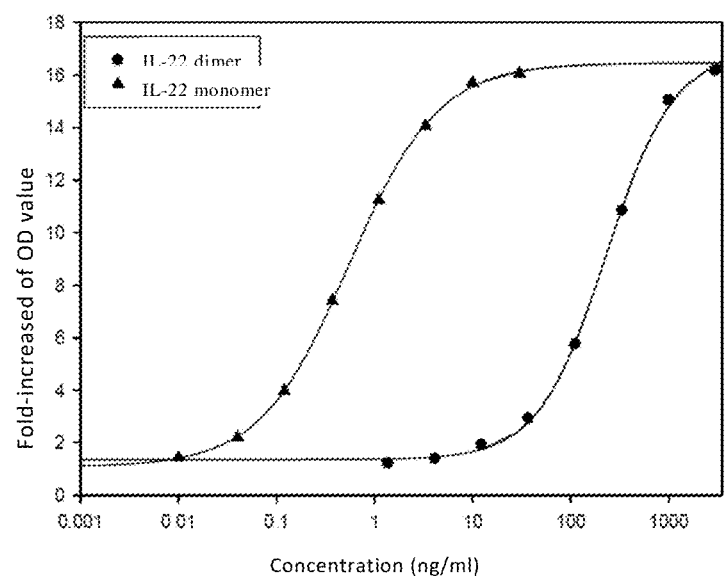

FIG. 8 shows the results of analysis on the in vitro bioactivity of IL-22 dimer and IL-22 monomer.

DETAILED DESCRIPTION OF THE PREFERRED EMBODIMENTS

Upon an extensive and in-depth study, the inventors have, for the first time ever, discovered that IL-22 has a significant therapeutic effect in virus induced hepatitis. IL-22 is shown to effectively protect the functions of liver and significantly reduce the elevation of blood ALT/AST caused by virus. In addition, as compared to IL-22 monomer, IL-22 dimer is shown to prolong in vivo half-life, improve pharmacokinetic properties of the drug thereof, reduce the injection frequency; especially, it is shown to enhance in vivo activity significantly and thus can treat viral hepatitis more effectively. This invention was made based on this discovery.

Terms

The term "essentially the same amino acid sequence" means that the amino acid sequence is identical; or that within the amino acid sequence, there is a change in one or more amino acid residues (missing, addition or replacement of one or more residues), and such change essentially would not decrease the biological activity thereof, in which the amino acid sequence can still express its biological function upon binding to IL-22 receptors in target cells. Any such "essentially the same" IL-22, either glycosylated (derived from natural or eukaryotic expression system) or un-glycosylated (derived from prokaryotic expression system or chemically synthesized), is within the scope of the present invention.

The term "therapy" refers to administration of IL-22 to a subject in need thereof in order to cure, ameliorate, improve, reduce or affect the disease, symptom, or predisposition of the subject.

The term "subject" refers to mice, human or other mammals.

The term "therapeutically effective dose" refers to a dose of IL-22 which can achieve the goal of treatment within the subject in need thereof. It is to be understood by one of ordinary skill in the art that, "therapeutically effective dose" may vary depending on the routes of administration, the types of excipients used and the combination with other medicaments.

IL-22 and the Method of Preparation Thereof

The term "Interleukin-22" or "IL-22" refers to a protein, which (a) has essentially the same amino acid sequence as the human/murine IL-22 as described by Dumoutier et al. in U.S. Pat. No. 6,359,117 and (b) the same biological activity as natural IL-22. IL-22 of the present invention includes but not limited to human IL-22, recombinant human IL-22, murine IL-22 and/or recombinant murine IL-22.

"IL-22" also includes pegylated IL-22 and covalently modified IL-22 proteins. For example, the IL-22 in the present invention can be polymerized by the modification with any activated polyethylene glycol (PEG) with molecular weight of 5,000-100,000 for the purpose of prolonging its half-life time. Detailed protocols can be referred in Greenwald et al., *Bioorg. Med. Chem. Lett.* 1994, 4, 2465; Caliceti et al., *IL Farmaco*, 1993, 48,919; Zalipsky and Lee, *Polyethylene Glycol Chemistry: Biotechnical and Biomedical Applications*, J. M. Harris, Plenus Press, New York (1992). Multi-arm branched PEG is preferred (CN ZL02101672.0, WO9932139, PCT/US95/0755, PCT/US94/13013, U.S. Pat. Nos. 4,640,835, 4,496,689, 4,301,144, 4,670,417, 4,791,192, 4,179,337).

IL-22 of the present invention is expressed by gene recombination technology. The expressed host cell includes prokaryotic cell, yeast or higher eukaryotic cell. Suitable prokaryotic host cell includes but not limited to G+ or G− bacteria, such as *E. coli*. Publicly available *E. coli* strains include K12 MM294 (ATCC 31,446), X1776 (ATCC 31,537), W3110 (ATCC 27,325) and K5 772 (ATCC 53,635), etc. Other suitable prokaryotic cells include but not limited to *Erwinia, Klebsiella, Proteus, Salmonella*, such as *Salmonella typhimurium, Serratia* such as *Serratia marcescans, Shigella, B. subtilis, B. licheniformis, Pseudomonas* such as *P. aeruginosa* and *Streptomyces*. *E. coli* W3110 is preferred since it is often used as the host cell for recombinant DNA product.

Apart from prokaryotic cells, eukaryotic cells such as filamentous fungi or yeast are also suitable for expression or cloning of IL-22 of the present invention. *Saccharomyces* is a common lower eukaryotic host microorganism. Other host cells include *Schizosaccharomyces pombe* (Beach and Nurse, Nature, 290:140 [ ]1981; EP 139,383); *Kluyveromyces* hosts (U.S. Pat. No. 4,943,529; Flee et al., Bio/Technology, 9:968-975 (1991)); such as *K. lactis* (MW98-8C, CBS683, CBS4574; Louvencourt et al., *J. Bacteriol.*, 154 (2):737-742 [1983]), *K. fragilis* (ATCC 12,424), *K. waltii* (ATCC 56,500), *K. drosophilarum* (ATCC 36,906; Van den Berg et al., *Bio/Technology*, 8:135 (1990)), *K. thermotolerans, K. marxianus*; yarrowia (EP 402,226); *Pichia Pastoris* (EP 183,070; Sreekrishna et al., J. Basic Microbiol., 28:265-278 [1988]); *Candida; Trichoderma reesia* (EP 244,234); *Neurospora crassa* (Case et al., Proc. Natl. Acad. Sci. USA, 76:5259-5263

[1979]); *Schwanniomyces* such as *Schwanniomyces occidentalis* (EP 394,538); filamentous fungi such as *Neurospora, Penicillium, Tolypocladium* (WO 91/00357), *Aspergillus* such as *A. nidulans* (Balance et al., *Biochem. Biophys. Res. Commun.*, 112:284-289[1983]; Tilburm et. al., *Gene*, 26:205-221 [1983]; Yelton et al., *Proc. Natl. Acad. Sci.* USA, 81: 1470-1474 [1984]) and *A. niger* (Kelly and Hynes, EMBO J., 4:475-479 [1985]). Methylotropic yeasts may also be used to express the IL-22 of the present invention, including but not limited to various types of yeast that can grow in methanol such as *Hansenula, Candida, Kloeckera, Pichia, Saccharomyces, Torulopsis, Rhodotorula*. Typical methylotroph can be found in C. Anthony, The biochemistry of Methylotrophs, 269 (1982).

Host cells used to express IL-22 of the present invention are mainly derived from multicellular organism. Examples of invertebrate cells include insect such as *Drosophila* S2 and Spodoptera Sf9, and plant cells. Suitable mammalian cells include Chinese Hamster Ovary (CHO), COS cells; in particular, SV40-transformed monkey kidney CV1 cell line (COS-7, ATCC CRL 1651); human embryo kidney cell line 293 (Graham et al., *J. Gen Virol.*, 36:59 (1997)); CHO/-DHFR (Urlaub and Chasin, *Proc. Natl. Acad. Sci.* USA, 77:4216 (1980)); murine testis trophoblastic cells (TM4, Mather, *Biol. Reprod.*, 23:243-251) (1980)); human lung cells (W138, ATCC CCL 75); human liver cells (Hep G2, HB 8065); murine breast cancer cells (MMT 060562, ATCC CCL51). One of ordinary skills in the art should be aware of how to select the suitable host cells.

The above mentioned host cells can be grown on conventional nutrient media after transformed or transfected with IL-22 expression vector or cloning vector. The aforesaid nutrient media, upon modification, is suitable for inducing promoter, selecting transformant or amplifying IL-22 encoding sequence. The conditions for nutrition such as selection of nutrient media, temperature and pH are clear to one of ordinary skills in the art. For the general principles for optimizing the proliferation of cultured cells, protocols and techniques thereof, see Mammalian Cell Biotechnology: a Practical Approach, M. Butler, ed. (IRL Press, 1991) and Sambrook et. al., supra.

The method of transfecting eukaryotic cells and transforming prokaryotic cells would be clear to one of ordinary skills in the art, such as method of using calcium chloride ($CaCl_2$), calcium phosphate precipitation, lipofectamine or electroporation. One skilled in the art would be able to select the suitable method depending on the different host cells used. For example, method of using $CaCl_2$ (Sambrook et al., supra.) or electroporation is generally suitable for eukaryotic cells; *agrobacterium tumefaciens* is mainly used for transforming plant cells (Shaw et. al., *Gene*, 23:315 (1983) and WO 89/05859); calcium phosphate precipitation may be used for those mammalian cells without cell walls (Graham and van der Eb, *Virology*, 52:456-457 (1978)). For a comprehensive description of the method for mammalian cells transfection, see U.S. Pat. No. 4,399,216. For techniques for yeast transfection, see Van Solingen et al., *J. Bact.*, 130:946 (1977) and Hsiao et al., *Proc. Natl. Acad. Sci.* (USA), 76:3829 (1979). Other techniques for introducing DNA into cells, such as nucleic acid micro-injection, electroporation, bacterial protoplast fusion with intact cells or polycations such as polybrene, polyornithine, etc. can be used in the present invention. For various techniques that can be used to transform mammalian cells, see Keown et al., *Methods in Enzymology*, 185: 527-537 (1990) and Mansour et al., *Nature*, 336:348-352 (1988).

The nucleotide sequence encoding IL-22 of the present invention can be inserted into a replicable vector for gene cloning or protein expression. All the vectors, such as plasmid, cosmid, virion or bacteriophage are publicly available. With the use of common techniques in this field, one skilled in the art can insert the nucleotide sequence encoding IL-22 into appropriate restriction endonuclease sites. A replicable vector usually includes but not limited to the following parts: one or more signal sequences, one origin of replication, one or more marker genes, one enhancer element, one promoter, and one transcription termination sequence. With the use of standard ligation techniques in this field, one skilled in the art can construct an appropriate replicable vector including one or more above parts.

The IL-22 of the present invention can not only be directly expressed through recombinant DNA, but also be produced through fusion of heterologous polypeptides. The later can be a signal sequence localized in a mature protein or an N-terminal of the polypeptide, and can also be other polypeptide fragments with specific digestion sites localized in a mature protein or an N-terminal of the polypeptide. Usually, the signal sequence is part of the above replicable vector, or part of the nucleotide sequence encoding IL-22 of the present invention inserted into a replicable vector. The signal sequence can be prokaryotic signal sequence, such as alkaline phosphatase, penicillinase, lpp, or the leader sequence of heat-stable enterotoxin II. In yeast secretion, the signal sequence can be yeast invertase leader sequence, a factor leader sequence (including a factor leader sequence of *Saccharomyces* or *Kluyveromyces* yeast, see U.S. Pat. No. 5,010, 182) or acid phosphatase leader sequence, leader sequence of glucose amylase of *C. albicans* (EP 362,179). In mammalian expression system, the mammalian signal sequence can be directly used in secreting the target protein. Such sequence includes signal sequence derived from the same or similar species of mammalians and secretion leader sequence of virus.

Both the expression vector and the cloning vector have a piece of nucleotide sequence, which enables the vector to replicate in one or more corresponding host cells. The nucleotide sequences corresponding with the bacteria, yeast or virus hosts are known to one of ordinary skills in the art. For example, the origin of replication of plasmid pBR322 is suitable for most $G^-$ bacteria, the origin of replication of 2.mu. Plasmid is suitable for yeast, while the origin of replication of viruses (SV40, polymoa virus, adenovirus, VSV or BPV) is suitable for cloning vector in mammalian cells.

Both the expression vector and the cloning vector have a piece of selecting gene, also referred to as "selecting marker". Typical protein expressed by selecting gene is (a) resistant to some antibiotics such as ampicillin, neomycin, methotrexate, tetracyclin etc, or toxin; (b) able to remedy auxotrophic deficiencies; and (c) supplemental to some key nutrient factors, such as D alanine racemase encoding sequence needed by bacillus hosts, that cannot be provided by complex media.

The selecting gene suitable for mammalian host cells should be able to distinguish the host cells that can accept IL-22 encoding gene of the present invention, such as DHFR or thymidine kinase. The suitable host cell using wild-type DHFR as the selecting gene is CHO strain without DHFR activity. The method of preparation and culture of this strain can be seen in Urlaub et al., *Proc. Natl. Acad. Sci.* USA, 77:4216 (1980). The selecting gene suitable for yeast cells is trp1 gene expressed in yeast plasmid Yrp7 (Stinchcomb et al., *Nature*, 282:39(1979); Kingsman et al., *Gene*, 7:141(1979); Tschemper et al., *Gene*, 10:157(1980)). trp1 gene can be used to screen yeast mutation strain that cannot grow on tryptophan, such as ATCC No. 44047 or PEP4-1 (Jones, *Genetics*, 85:12 (1977)).

Both expression vector and clone vector usually include a promoter that can be manually ligated to the nucleotide sequence encoding IL-22 of the present invention, for directing mRNA synthesis. Promoters corresponding to all kinds of hosts are known to one skilled in the art. The promoters suitable for prokaryotic hosts include β-lactamase and lactose promoter system (Chang et al., *Nature*, 275:615 (1978); Goeddel et al., *Nature*, 281; 544 (1979)), alkaline phosphatase and trp promoter system (Goeddel, *Nucleic Acids Res.*, 8:4057 (1980); EP 36,776), hetero-promoter such as tac promoter (deBoer et al., *Proc. Natl. Acad. Sci.* USA, 80:21-25 (1983)). Bacterial host promoter also includes a piece of Shine-Dalgarno (SD) sequence that can be manually ligated to the nucleotide sequence encoding IL-22 of the present invention.

Promoters suitable for yeast host include 3-phosphoglyceric kinase promoter (Hitzeman et al., *J. Biol. Chem.*, 255: 2073(1980)) or other glycolytic enzyme promoters (Hess et al., *J. Adv. Enzyme Reg.*, 7:149 (1968); Holland, Biochemistry, 17:4900 (1978)), such as enolase, glyceraldehydes-3-phosphate dehydrogenase, hexokinase, pyruvate decarboxylase, fructose kinase, glucose-6-phosphate isomerase, triphosphoglycerate mutase, pyruvate kinase, triose phosphate isomerase, glucose phosphate isomerase and glucose kinase.

Some other inducible yeast promoters can regulate transcription according to different growing conditions, including promoters for alcohol dehydrogenase 2, isocytochrome C, acid phosphatase, degrading enzymes related to nitrogen degradation, metallothionein, glyceraldehyde-3-phosphate, degrading enzymes of maltose and galactose. Detailed description of vectors and promoters suitable for yeast expression system can be seen in EP 73,657.

Promoters can control the transcription of IL-22 gene sequence of the present invention on the replicable vector in mammalian host cells. These promoters include those from certain viral genome such as polymoa virus, Fowlpox virus (UK 2,211,504), adenovirus, bovine papilloma virus, avian sarcoma virus, cytomegalovirus, retrovirus, hepatitis B virus, or SV40; those from foreign mammalian such as β-actin promoter or immunoglobulin promoter; and those from heat shock protein promoter. However, these promoters should be compatible with the expression system of the host.

The transcription of the IL-22 encoding nucleotide sequence of the present invention in eukaryotic expression system can be enhanced through the insertion of enhancer into the replicable vectors. Enhancer is a type of cis-acting element of DNA molecule and is usually of the length of 10-300 bp, which can enhance the transcription of DNA molecules by acting on the promoters. Currently, it is known that there are a number of enhancers originated from mammalian gene (haptoglobin, elastase, albumin, α-fetoprotein and insulin). The most widely used enhancers are from eukaryotic viral cells, such as SV 40 enhancer (100-270 bp) at the late side of the origin, enhancer of cytomegalovirus early promoter, polymoa virus enhancer at the late side of the origin, and adenovirus enhancer. The enhancers can be inserted into the 5' or 3' terminal of the IL-22 encoding sequence of the present invention on the replicable vectors, but the 5' terminal is preferred.

The expression vectors in eukaryotic host cells (yeast cells, fungi cells, insect cells, plant cells, animal cells, human cells, or other nucleated cells from other multicellular organisms) also include the nucleotide sequence for terminating transcription and stabilizing mRNA. This type of sequence is usually derived from the 5' terminal of untranslated region in eukaryotic cells, viral DNA or cDNA, and is sometimes derived from the 3' terminal. The nucleotide sequence within "the untranslated region" can be transcribed as acylated polyA sequence at the untranslated region of IL-22 of the present invention.

Other methods, vectors and host cells for synthesizing the IL-22 of the present invention in recombinant vertebrate culture system can be seen in Gething et al., *Nature*, 293:620-625 (1981); Mantei et al., *Nature*, 281:40-46 (1979); EP 117,060 and EP 117,058.

IL-22 Dimer

Figure 1:
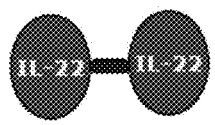
FIG. 1 illustrates the structure of an IL-22 dimer of the present invention in which "—" represents the linker and the oval-shaped object labeled with "IL-22" represents an IL-22 monomer.

The structure of the IL-22 dimer of the present invention is shown in Formula I. FIGS. 1-3 illustrate the representative structure of the IL-22 dimer of the present invention, in which the carrier protein includes but not limited to Fc fragment of human IgG (1, 2, 3, 4), or human albumin IL-22 can be localized at the C-terminal or N-terminal of the carrier protein.

As used herein and in the claims, "linker" refers to a short peptide connecting the two IL-22 monomers and being disposed therebetween. There is no special restriction on the length of the linker. A linker is usually 5-50 amino acid residues in length. In general, a linker does not affect or significantly affect the proper fold and conformation formed by the configuration of the two IL-22 monomers. Examples of linker include but not limited to:

In a further preferred embodiment, the linker comprises amino acid sequence selected from the group consisting of:

(a). an amino acid sequence with 3-16 amino acid residues formed by hydrophobic amino acids glycine (Gly) or proline (Pro), such as Gly-Pro-Gly-Pro-Gly-Pro;

(b). an amino acid sequence encoded by multiple cloning sites. Such sequence usually contains 5-20 amino acid residues; in a preferred embodiment, such sequence contains 10-20 amino acid residues;

(c). an amino acid sequence comprising protein(s) not from IL-22 monomer, such as an amino acid sequence of IgG or albumin; and (d). an amino acid sequence comprising any combination of (a), (b), and (c) above.

In one preferred embodiment, the linker has the sequence of GSGGGSGGGGSGGGGS (i.e. 147-162 amino acid residues of SEQ ID NO:1) and ASTKGP (i.e. 147-152 amino acid residues of SEQ ID NO:3).

Besides, an amino acid sequence not affecting the biological activity of IL-22 monomer can be added to the N-terminal or C-terminal of the fusion protein. In a preferred embodiment, such appended amino acid sequence is beneficial to expression (e.g. signal peptide), purification (e.g. 6× His sequence, the cleavage site of *Saccharomyces cerevisiae* α-factor signal peptide (Glu-Lys-Arg)), or enhancement of biological activity of the fusion protein.

Preparation Method of Dimer

The encoding of the DNA sequences of the IL-22 dimer or the fusion protein of the present invention can be entirely synthesized artificially. Alternatively, the encoded DNA sequences of the first IL-22 monomer and/or the second IL-22 monomer can be obtained by PCR amplification or synthesis and then joined together to form the encoded DNA sequence of the IL-22 dimer or fusion protein of the present invention.

In order to enhance the expression volume of the host cells, modification can be performed on the encoded sequence of IL-22 dimer. For example, codon bias of host cells can be used to eliminate sequences that are not beneficial to transcription and translation. In the present invention, codon bias of yeast cells or mammalian cells can be used in combination with DNA software for detecting genes of IL-22 dimer so as to eliminate sequences that are not beneficial to transcription and translation. The eliminated sequences can be intron cutting site, transcription terminating sequence, etc.

After the encoded DNA sequence of the novel fusion protein of the present invention is obtained, it is first inserted into an appropriate expression carrier, followed by an appropriate host cell. Finally, the transformed host cell is cultivated and purified to obtain the novel fusion protein of the present invention.

As used herein and in the claims, "carrier" refers to plasmid, cosmid, expression vector cloning vector, virus vector, etc.

In the present invention, carrier known in the art, such as carriers available in the market, can be used. For example, with the use of carrier obtained from the market, encoded nucleotide sequence of the novel fusion protein of the present invention is operationally connected to the expressing and controlling sequence to form the protein-expressing carrier.

As used herein and in the claims, "operationally connected" refers to a scenario that some parts of a linear DNA sequence can affect the biological activity of other parts of the same linear DNA sequence. For instance, if signal DNA is used as the expression of a precursor and participates in secretion of polypeptides, the signal DNA (secretion leader sequence) is "operationally connected" to the polypeptides. If a promoter controls sequence transcription, the promoter is "operationally connected" to the encoded sequence. If a ribosome binding site is situated at a position where translation thereof is made possible, the ribosome binding site is "operationally connected" to the encoded sequence. In general, "operationally connected" means that the concerned residues are in proximity; for secretion leader sequence, "operationally connected" refers to proximity within the reading frame.

As used herein and in the claims, "host cells" refers to both prokaryotic cells and eukaryotic cells. Prokaryotic host cells commonly used include *E. coli, B. subtilis*, etc. Eukaryotic host cells commonly used include yeast cells, insect cells, and mammalian cells, etc. In a preferred embodiment, the host cells used are eukaryotic cells; in another preferred embodiment, the host cells used are mammalian cells.

After the transformed host cells are obtained, they can be cultivated under an environment suitable to express the fusion protein of the present invention for expressing the fusion protein. The expressed fusion protein is then separated.

Pharmaceutical Composition and Method of Administration Thereof

Since the IL-22 dimer of the present invention can generate a stronger receptor activation signal and has an excellent serum half-life, the IL-22 dimer and a pharmaceutical composition comprising the IL-22 dimer as the main active ingredient can be used for treating viral hepatitis. In a preferred embodiment, the viral hepatitis comprises: hepatitis A, hepatitis B, hepatitis C, hepatitis D, and hepatitis E.

The pharmaceutical composition of the present invention comprises a safe and effective amount of the IL-22 dimer of the present invention and a pharmaceutically acceptable excipient or carrier. "Safe and effective amount" refers to an amount of a compound sufficient to significantly improve the condition of the patient in need thereof, without causing serious side-effects. In general, the pharmaceutical composition comprises 0.001-1,000 mg of IL-22 or its dimer per dose; in a preferred embodiment, the pharmaceutical composition comprises 0.05-300 mg of IL-22 or its dimer per dose; in a further preferred embodiment, the pharmaceutical composition comprises 0.5-200 mg of IL-22 or its dimer per dose.

"Pharmaceutically acceptable excipient or carrier" refers to a solid or liquid filler or gelatin material with one or more types of compatibilities which is suitable to be used in human with sufficient purity and sufficiently low toxicity. "Compatibility" refers to the ability of each ingredient of the composition to mutually blend with the compound of the present invention and the ability to mutually blend therebetween, without substantially decreasing the clinical efficacy of the compound. Some of the examples of pharmaceutically acceptable excipient or carrier include cellulose and its derivatives (e.g. sodium carboxymethylcellulose, sodium ethylcellulose, cellulose acetate, etc), gelatin, speckstone, solid lubricating agent (e.g. stearic acid, magnesium stearate), calcium sulphate, plant oil (e.g. pea oil, sesame oil, peanut oil, olive oil, etc.), polyols (e.g. propylene glycol, glycerol, mannitol, sorbitol, etc.), emulsifier (e.g. Tween®), wetting agent (e.g sodium lauryl sulfate), colorant, flavoring agent, stabilizer, anti-oxidant, antiseptic, pyrogen-free water, etc.

Route of administration of the IL-22 or its dimer of the present invention comprises oral administration, rectal administration, parenteral administration (intravenous, intramuscular, or subcutaneous), and partial administration.

Solid form for oral administration comprises capsules, tablets, pills, powder, and granules. In these solid forms, active compound is mixed with at least one of the conventionally inert excipients (or carriers), such as sodium citrate, dicalcium phosphate, or any of the following ingredients: (a) filing or bulking agent, e.g. starch, lactose, sucrose, glucose, mannitol, and silicic acid; (b) adhesion agent, e.g. carboxymethylcellulose, alginate, gelatin, polyvinyl pyrrolidone, sucrose, and acacia; (c) humectants, e.g. glycerol; (d) disintegrating agent, e.g. agar, calcium carbonate, potato starch or cassava starch, alginic acid, compounded silicate, and sodium carbonate; (e) buffering agent, e.g. paraffin wax; (f) absorption accelerating agent, e.g. quaternary amine compound; (g) wetting agent, e.g. cetanol and glycerin monostearate; (h) absorbent, e.g. bolus alba; and (i) lubricant, e.g. speckstone, calcium stearate, sodium stearate, solid polyethylene glycol, sodium lauryl sulfate, or any mixture thereof. Capsules, tablets, and pills can also comprise buffering agent.

Solid form such as tablets, sugar pills, capsules, pills, and granules can be prepared with coating and core-shell materials, such as casing and other materials known in the art. These materials comprise opacifying agent and the active compound or compound in the composition that can be released in a delayed fashion at a certain part of the alimentary canal. Embedding component such as polymer materials and wax materials can be used. If necessary, active compounds can be mixed with one or more of the above-described excipients to formulate a micro capsule form.

Liquid form for oral administration comprises pharmaceutically acceptable emulsion, solution, suspension, syrup, or tincture. Apart from active compounds, liquid form also comprises inert diluents conventionally used in the art such as water or other solvent, solublilizing agent and emulsifier such as ethanol, isopropanol, carbonate acetate, ethyl acetate, propan-2-ol, 1,3-butan-2-ol, dimethylformamide, and oil; in particular cotton seed oil, peanut oil, maize embryo oil, olive oil, castor oil, and sesame oil, or any mixtures thereof.

Apart from the inert diluents, the compound can also comprise additives, such as wetting agent, emulsifying agent, suspending agent, sweetening agent, correctives, and spices.

Apart from the active compounds, suspension can also comprise suspending agent, such as ethoxyl isostearic alcohol, polyoxyethylene sorbitol, sorbitan, microcrystalline cellulose, aluminium methoxide, agar, or any mixtures thereof.

Compounds used for parenteral administration can also comprise physiologically acceptable sterile water or anhydrous solution, dispersion solution, suspension, or emulsion, and sterile powder that can be re-dissolved into sterile injectable solution or dispersion solution. Suitable hydrated or anhydrous carriers, diluting agent, solvent, or excipient comprises water, ethanol, polyols, and suitable mixtures thereof.

Forms of the IL-22 dimer of the present invention used for partial administration comprise ointment, powder, patch, sprayer, and inhalant. Under sterile conditions, the active components can be mixed with physiologically acceptable carrier and any antiseptics, buffering agents; if necessary, the active components may be mixed with propellant.

The IL-22 dimer of the present invention can be solely administrated or be administrated in conjunction with any pharmaceutically acceptable compounds.

The micro-capsule containing IL-22 or its dimer of the present invention can be used as a sustained release system. Sustained release micro-capsule system of recombinant protein has been successfully applied to rhGH, rhIFN, IL-2 and MNrgp120 (Johnson et al., Nat. Med., 2:795-799 (1996); Yasuda, Biomed. Ther 27:1221-1223 (1993); WO 97/03692, WO 96/40072, WO 96/07399; U.S. Pat. No. 5,654,010).

The sustained release system of IL-22 or its dimer of the present invention can be prepared with PLGA which has good biologically compatibility and degradability. Lactic acid and glycolic acid, the degrading products of PLGA, can be cleared quickly in human body. Furthermore, the degradability of that polymer can vary from several months to several years depending on its molecular weight and composition (Lewis, "Controlled release of bioactive agents form lactide/glycolide polymer," in: M. Chasin and R. Langer (Eds.), Biodegradable Polymers as Drug Delivery Systems (Marcel Dekker: New York, 1990), pp. 1-41)).

The dosage and concentration of the pharmaceutical composition of the present invention can be adjusted according to actual situation. One skilled in the art should know how to choose the suitable dosage and injection means according to practical needs. The principle for adjusting between different species such as mice and human can be seen in Mordenti, J. and Chappell, W. "*The use of interspecies scaling in toxicokinetics*" In Toxicokinetics and New Drug Development, Yacobi et al.; Pergamon Press, New York 1989, pp. 42-96.

On using the pharmaceutical composition, a safe and effective amount of the IL-22 dimer of the present invention is administrated to a mammal (e.g. human) in need thereof, in which the dosage administrated is a pharmaceutically acceptable effective administration dosage. For a human of 60 kg, the administration dosage is usually 0.01-300 mg; in a preferred embodiment, the administration dosage is 0.5-100 mg. In determination of the actual dosage, factors known in the art such as administration route, condition of the patients, etc. have to be considered.

There are many advantages of the present invention including but not limited to the following:

1. IL-22 or its dimer has been proven to be effective in treating viral hepatitis in animal models.

2. IL-22 dimer can prolong in vivo half-life, improve pharmacokinetic properties of the drug thereof, reduce the injection frequency, and significantly enhance in vivo bioactivity.

3. At equal IL-22 molar ratio, IL-22 dimer is also shown to exhibit stronger in vivo STAT3 activation signal as compared to IL-22 monomer, thereby enhancing the therapeutic effect.

The following exemplary embodiments further describe the present invention. Although the description referred to particular embodiments, it will be clear to one skilled in the art that the present invention may be practiced with variation of these specific details. Hence this invention should not be construed as limited to the embodiments set forth herein.

Further, for the embodiments in which details of the experimental methods are not described, such methods are carried out according to conventional conditions such as those described in Sambrook et al. Molecular Cloning: A Laboratory Manual (New York: Cold Spring Harbor Laboratory Pres, 1989), or suggested by the manufacturers.

Example 1

The IL-22 dimer with the structure described in FIGS. 1-3 is prepared and purified by conventional methods. SEQ ID NO:1 represents IL-22 dimer and SEQ ID NOs:2-5 represent IL-22 monomer with Fc fragments.

Example 2

In Vivo Half-Life of IL-22 Dimer

Rats received a single subcutaneous injection of IL-22 dimer (which is formed by two IL-22 monomers of SEQ ID NO: 2) with a dosage of 100 µg/kg. The pharmacokinetic parameters (n=6) were calculated and listed in Table 1 below. The in vivo half-life of IL-22 monomer in rats is about 1.3 hours.

| Parameter | Unit | Average Value | SD |
|---|---|---|---|
| $AUC_{(0-t)}$ | ng/mL * h | 4216.7 | 638.3 |
| $MRT_{(0-t)}$ | h | 22.6 | 1.6 |
| $t_{(1/2)}$ | h | 7.8 | 1.3 |
| Clz/F | L/h/kg | 0.028 | 0.003 |
| $C_{max}$ | ng/mL | 153.2 | 26.2 |

Example 3

Effect of IL-22 or its Dimer on Liver pSTAT3 of Mice 52 normal ICR mice in which half of them were male with weight of 20-22 g were tested. The mice were divided into 13 groups with 4 mice per group. One group of mice was sacrificed before the administration of the drug and the liver tissues were removed and stored in liquid nitrogen for determining the basic level of phosphorylation of STAT3 (pSTAT3) of the liver. 6 groups of mice received single subcutaneous injection of recombinant IL-22 at a dosage of 40 µg/kg; while another 6 groups of mice received single subcutaneous injection of equimolar doses of recombinant IL-22 dimer at dosage of 100 µg/kg (the IL-22 dimer was formed by two IL-22-Fc monomers with a sequence as shown in SEQ ID NO: 4, wherein the IL-22 in one mole of the dimer is calculated as 2 moles). After injection, the liver tissue were respectively removed at the $2^{nd}$, $4^{th}$, $8^{th}$, $24^{th}$, $48^{th}$, $72^{nd}$ hour and stored in liquid nitrogen. Then liver tissue homogenate was prepared and the protein content thereof was determined. The pSTAT3 level was detected by the ELISA method (STAT3 [pY705] phosphor ELISA Kit, Invitrogen Corporation).

As shown in FIG. 4, the injection of IL-22 (40 µg/kg) into normal mice can significantly increase the level of liver pSTAT3 in which the level was at the maximum at around the $2^{nd}$ hour and resumed to the basic level at the $8^{th}$ hour. Injection of IL-22 dimer (100 µg/kg), at equimolar dose of IL-22, into normal mice can significantly increase the level of liver pSTAT3, in which the level reached a maximum around the $24^{th}$ hour, remained relatively high at the $48^{th}$ hour, and basically recovered to the basic level at the $72^{nd}$ hour.

As illustrated by the aforesaid result, both IL-22 and IL-22 dimer can activate the biological activity of the signal transduction and activator of transcription factor 3 (STAT3).

It is worthwhile to note that, at equimolar dose of IL-22, the biological activity of the IL-22 dimer was significantly better than the biological activity of the IL-22 monomer.

Example 4

Effect of IL-22 or its Dimer in the Treatment of Virus-Induced Hepatitis in Mice 50 female C57/BL mice aged 6-8 weeks were divided into 5 groups with 10 mice per group. Four groups of mice were injected intraperitoneally with MHV-A59 virus at a dose of $2\times10^4$ pfu per mouse. Preparation and titration of MHV-A59 can be referred in Chin J Clin Pharmacol Ther 2005, 10(11): 1253. 2 hours after the virus injection, the treatment group received subcutaneous injection with recombinant human IL-22 at a dose of 100 μg/kg once every day; or with pegylated IL-22 at a dose of 100 μg/kg once every other day; or with recombinant IL-22 dimer (IL-22-IgG-Fc fusion protein) (the IL-22 dimer was formed by two IL-22-Fc monomers with a sequence shown in SEQ ID NO: 2, wherein the IL-22 in one mole of the dimer is calculated as 2 moles) at a dose of 100 μg/kg once every other day. The recombinant human IL-22 group received a total of 5 injections, while the pegylated human IL-22 group and the recombinant human IL-22 dimer treatment group respectively received a total of 3 injections. The negative control group 1 included normal C57/BL female mice and the negative control group 2 included MHV-A59 virus infected mice which received injection of solvent carrier (0.5% mouse serum, PBS, pH 7.0). Prior to the virus injection, two animals were taken from each group and 100 μL of blood was collected from the orbit for determination of ALT, AST levels as the baseline. 3 days and 5 days after the infection of MHV-A59 virus, blood samples were collected from each group for determination of ALT, AST levels. On the $5^{th}$ day, 2% pentobarbital was used to anesthetize the animals and the livers were separated and fixed with 4% formalin for biopsy and HE staining.

As shown in FIGS. 5-7, daily injection of recombinant human IL-22 monomer (IL-22 or pegylated IL-22) and IL-22 dimer can suppress the multi-fold increase of ALT/AST caused by the hepatitis virus, reduce the chance of liver inflammation and hepatocellular necrosis, and protect liver cells from damage caused by hepatitis virus.

It is worthwhile to note that, at converted equimolar dose of IL-22, the therapeutic effect is IL-22 dimer>pegylated IL-22>IL-22. In other words, the therapeutic effect on viral hepatitis in mice injected with IL-22 dimer was not only much better than the group of animals injected with IL-22 monomer, but also better than the group of animals injected with pegylated IL-22 monomer with longer half-life. Therefore, the therapeutic effect of IL-22 dimer was significantly better than IL-22 monomer and pegylated IL-22. The protein molecular weight ratio of IL-22 monomer or pegylated IL-22 to IL-22 dimer is about 1:5. Therefore, under the condition that the IL-22 molecular administration molar dose is lower than that of IL-22 or pegylated IL-22, IL-22 dimer showed a more significant therapeutic effect

Example 5

Formation of IL-22 Dimer by IL-22-Fc Complex a. Construction of IL-22 Dimer Expression Cell Line The cDNA sequences encoding IL-22-Fc complexes (as shown in SEQ ID NO: 6 or SEQ ID NO: 7, in which SEQ ID NO: 6 encodes the monomer shown in SEQ ID NO: 2, SEQ ID NO.: 7 encodes the monomer shown in SEQ ID NO: 3) were synthesized. The cDNA sequence of human IL-22 monomer was connected with the cDNA sequence of fragments of IgG2 Fc. EcoRI site and components required for mammalian cell expression such as Kozak sequence and signal peptide sequence were introduced at the 5' end, while XbaI site was introduced at the 3' end. It was cloned into a commercially available pUC19 plasmid and named as pIL-22-Fc, and transformed into E. coli TG1. pIL-22-Fc plasmid was digested by EcoRI and XbaI, and approximately 1300 bp of IL-22-Fc fragment were harvested and connected with EcoRI and XbaI digested expression plasmid pcDNA3 (Invitrogen) to construct expression plasmid pEX-IL-22-Fc. Expression plasmid pEX-IL-22-Fc was linearized and transfected into CHO cells to express IL-22 dimer. The expression level was detected by ELISA method and cell lines with a higher protein yield were screened and cell library was prepared.

b. Separation and Purification of IL-22 Dimer

Recombinant CHO cells were cultured by conventional method to express recombinant protein. After cell culture, the cell supernatant was harvested (containing IL-22 complexes, IL-22 dimers, IL-22 multimers and metabolites). The collected supernatant was filtered and purified by a series of chromatography methods. For example, it was captured by rProtein A Sepharose FF (GE Healthcare, cat #17-1279-04), and eluted with a 20-50 mM citrate buffer and 0.1-2M NaCl at pH 3.5-3.8 to obtain IL-22 dimer of purity greater than 90%, then the next step was performed by using mixed-mode PPA chromatography (PALL Life Sciences Cat #: k364-01) and the target protein was eluted with a buffer solution of 20-50 mM NaAc/HAC at pH 3.0-5.0. In this process, low pH inactivation and Nano 20 membrane filtration were used for viral removal. IL-22 dimer was ultimately obtained.

The purity of the purified IL-22 dimer was greater than 95% (using reverse phase HPLC analysis). As illustrated by electrophoresis, the molecular weight of the purified IL-22 dimer (formed by two monomers shown in SEQ ID NO: 2) was 52±10 KD (using reduced SDS-PAGE analysis) which matched with the predicted value. The maximum UV absorption wavelength is 280 nm IL-22 dimers can stimulate Colo205 cells to produce IL-10 in vitro. (ED50 is 10-1000 ng/mL)

Example 6

Pharmacokinetics IL-22 Dimer in Rhesus Monkeys 8 adult healthy rhesus monkeys in which half of them were male with weight of 3-5 kg were randomly divided into 2 groups according to the weight of the animal. The groups were treated with IL-22 dimer at a dose of 30 or 100 μg/kg in which each treatment group had 4 animals, half of them were male. Each group received subcutaneous injection of the corresponding dose of IL-22 dimer (formed by two monomers shown in SEQ ID NO: 2) at the administration volume of 0.2 ml/kg body weight in single administration. 0.6 mL blood was collected at the saphenous veins of the lower extremity prior to the administration and at the half, $1^{st}$, $2^{nd}$, $4^{th}$, $8^{th}$, $16^{th}$, $48^{th}$, $72^{nd}$, $96^{th}$, $120^{th}$, $144^{th}$, $168^{th}$ hour after administration and upon standing at room temperature for 30 min, the serum was separated and the serum IL-22 dimer concentration was detected using an ELISA kit (Biolegend, Cat #434507). Pharmacokinetic parameters were analyzed using a non-compartmental model on the detected results, and the the results were shown in Table 1. In vivo half-life (t1/2z) of IL-22 is about 2 hr.

TABLE 1

| Dose | AUC(0-t) mg/L*hr | MRT(0-t) hr | t½z hr | Tmax hr | CLz/F mL/h/kg | Cmax ng/mL |
|---|---|---|---|---|---|---|
| 30 μg/kg | 11.92 ± 0.91 | 50.5 ± 5 | 63.3 ± 38.9 | 17 ± 9.5 | 2 ± 1 | 172.3 ± 17.1 |
| 100 μg/kg | 39.9 ± 6.2 | 51.1 ± 4.7 | 65.6 ± 10.9 | 24 ± 0 | 2 ± 0 | 506.9 ± 115.7 |

Pharmacokinetic parameters (average ± SD, n = 4)

Example 7

In Vitro Bioactivity Analysis of IL-22 Dimer and IL-22

Colo205 cells were cultured in RPMI1640 10% FBS medium and the cells were grown to the logarithmic phase. Supernatant was discarded and PBS was added to wash away residual culture medium, followed by addition of 2~5 mL 0.25% Trypsin-EDTA for digestion. Then medium was added and mixed to uniformity. Mixture was centrifuged at 1500 rpm for 5 min and cells were collected and prepared into $5.0 \times 10^5$ Cell/ml cell suspension with basic medium. The suspension was added into the wells of 96-well plate (100 μL/well) and stayed overnight at 37° C., in 5% $CO_2$ incubator. On the next day, the 96-well plate was removed from the $CO_2$ incubator and centrifuged at 800 rpm for 5 minutes at 4'C. Then, 90 μL of cell supernatant was withdrawn from each well and added with 90 μL 0.1% BSA/RPMI1640, followed by addition of IL-22 dimer (formed by two monomers shown in SEQ ID NO: 2) to the final concentration of 1.4, 4.1, 12.3, 37.0, 111.1, 333.3, 1000, 3000 ng/mL, IL-22 to the final concentration of 0.01, 0.04, 0.12, 0.37, 1.1, 3.3, 10, 30 ng/mL. The mixture was incubated for 20 hours in 5% $CO_2$ incubator and cell supernatant was collected and the OD value thereof was tested using IL-10 ELISA kit (R&D Cat#S1000B). As shown in FIG. 8, the ED50 value of IL-22 dimer is 229 ng/mL (2675 pM) and that of IL-22 is 0.54 ng/mL (32.4 pM).

As shown in the results above, although in vitro bioactivity of IL-22 is slightly better than that of the IL-22 dimer, in vivo pharmacokinetic parameters and effect of IL-22 dimer are better than those of IL-22. Hence, in vivo models should be used for evaluating the biological activity IL-22 dimers.

All references mentioned in the present invention are cited herein by reference. Although the description referred to particular embodiments, it will be clear to one skilled in the art that the present invention may be practiced with variation of these specific details. Hence this invention should not be construed as limited to the embodiments set forth herein.

What is claimed is:

1. A polypeptide comprising interleukin 22 (IL-22) and an Fc-fragment of human IgG2, wherein the polypeptide comprises the amino acid sequence of SEQ ID NO:2.

2. A polypeptide comprising interleukin 22 (IL-22) and an Fc-fragment of human IgG2, wherein the polypeptide comprises the amino acid sequence of SEQ ID NO:3.

3. A polypeptide comprising interleukin 22 (IL-22) and an Fc-fragment of human IgG2, wherein the polypeptide comprises the amino acid sequence of SEQ ID NO:4.

4. An interleukin 22 (IL-22) dimer comprising two IL-22 monomers of a polypeptide comprising IL-22 and an Fc fragment of human IgG2, wherein the Fc fragment comprises amino acid residues 163-385 of SEQ ID NO:2.

5. The interleukin 22 (IL-22) dimer of claim 4, wherein the IL-22 monomers are connected via a disulfide bond.

6. The interleukin 22 (IL-22) dimer of claim 5, wherein the IL-22 monomers are connected by two to four disulfide bonds.

7. The interleukin 22 (IL-22) dimer of claim 6, wherein the IL-22 dimer retains the biological activity of IL-22 and has a serum half-life of at least twice of the half-life of the IL-22 monomer.

8. A pharmaceutical composition comprising the interleukin 22 (IL-22) dimer of claim 4, further comprising a pharmaceutically acceptable carrier.

* * * * *